US008423320B2

(12) United States Patent
Schaller et al.

(10) Patent No.: US 8,423,320 B2
(45) Date of Patent: Apr. 16, 2013

(54) METHOD AND SYSTEM FOR QUANTITATIVE INLINE MATERIAL CHARACTERIZATION IN SEMICONDUCTOR PRODUCTION PROCESSES BASED ON STRUCTURAL MEASUREMENTS AND RELATED MODELS

(75) Inventors: Matthias Schaller, Boxdorf (DE); Thomas Oszinda, Dresden (DE); Christin Bartsch, Stolpen (DE); Daniel Fischer, Dresden (DE)

(73) Assignee: Advanced Micro Devices, Inc., Austin, TX (US)

( * ) Notice: Subject to any disclaimer, the term of this patent is extended or adjusted under 35 U.S.C. 154(b) by 287 days.

(21) Appl. No.: 12/417,787

(22) Filed: Apr. 3, 2009

(65) Prior Publication Data

US 2009/0319196 A1    Dec. 24, 2009

(30) Foreign Application Priority Data

Jun. 20, 2008   (DE) .......................... 10 2008 029 498

(51) Int. Cl.
   *G01B 11/00*   (2006.01)
(52) U.S. Cl.
   USPC ............... 702/172; 702/31; 702/40; 702/155; 702/159
(58) Field of Classification Search .................... 702/31, 702/36, 23, 35, 40, 81, 83, 134, 135, 155, 702/159, 172; 438/7, 16; 257/E21.53, E21.525
   See application file for complete search history.

(56) References Cited

U.S. PATENT DOCUMENTS

| | | | |
|---|---|---|---|
| 5,094,984 A * | 3/1992 | Liu et al. ........................ | 438/760 |
| 6,858,454 B1 | 2/2005 | Kanzawa et al. ............... | 438/16 |
| 7,333,200 B2 | 2/2008 | Sezginer et al. ............... | 356/401 |
| 2003/0094032 A1* | 5/2003 | Baklanov et al. .................. | 73/38 |
| 2004/0023403 A1 | 2/2004 | Tatsunari ...................... | 436/144 |
| 2004/0110310 A1 | 6/2004 | Sun et al. ............................ | 438/5 |
| 2004/0229388 A1* | 11/2004 | Guldi et al. ...................... | 438/14 |
| 2004/0267490 A1* | 12/2004 | Opsal et al. ................... | 702/127 |
| 2007/0012337 A1* | 1/2007 | Hillman et al. ................. | 134/1.3 |
| 2007/0260132 A1* | 11/2007 | Sterling ........................ | 600/336 |

OTHER PUBLICATIONS

Translation of Official Communication from German Patent Office for German Patent Application No. 10 2008 029 498.5 dated Feb. 23, 2009.

* cited by examiner

*Primary Examiner* — Mohamed Charioui
*Assistant Examiner* — Paul D Lee
(74) *Attorney, Agent, or Firm* — Williams, Morgan & Amerson, P.C.

(57) ABSTRACT

By using powerful data analysis techniques, such as PCR, PLS, CLS and the like, in combination with measurement techniques providing structural information, gradually varying material characteristics may be determined during semiconductor fabrication, thereby also enabling the monitoring of complex manufacturing sequences. For instance, the material characteristics of sensitive dielectric materials, such as ULK material, may be detected, for instance with respect to an extension of a damage zone, in order to monitor the quality of metallization systems of sophisticated semiconductor devices. The inline measurement data may be obtained on the basis of infrared spectroscopy, for instance using FTIR and the like, which may even allow directly obtaining the measurement data at process chambers, substantially without affecting the overall process throughput.

26 Claims, 8 Drawing Sheets

METHOD AND SYSTEM FOR QUANTITATIVE INLINE MATERIAL CHARACTERIZATION IN SEMICONDUCTOR PRODUCTION PROCESSES BASED ON STRUCTURAL MEASUREMENTS AND RELATED MODELS

BACKGROUND OF THE INVENTION

1. Field of the Invention

The present disclosure generally relates to the field of fabricating semiconductor devices, and more particularly, to process control and monitoring techniques for manufacturing processes on the basis of optical measurement strategies.

2. Description of the Related Art

Today's global market forces manufacturers of mass products to offer high quality products at a low price. It is thus important to improve yield and process efficiency to minimize production costs. This holds especially true in the field of semiconductor fabrication, since, here, it is essential to combine cutting-edge technology with volume production techniques. It is, therefore, the goal of semiconductor manufacturers to reduce the consumption of raw materials and consumables while at the same time improve product quality and process tool utilization. The latter aspect is especially important since, in modern semiconductor facilities, equipment is required which is extremely cost-intensive and represents the dominant part of the total production costs. For example, in manufacturing modern integrated circuits, several hundred individual processes may be necessary to complete the integrated circuit, wherein failure in a single process step may result in a loss of the complete integrated circuit. This problem is even exacerbated in current developments striving to increase the size of substrates, on which a moderately high number of such integrated circuits are commonly processed, so that failure in a single process step may possibly entail the loss of a large number of products.

Therefore, the various manufacturing stages have to be thoroughly monitored to avoid undue waste of man power, tool operation time and raw materials. Ideally, the effect of each individual process step on each substrate would be detected by measurement and the substrate under consideration would be released for further processing only if the required specifications, which would desirably have well-understood correlations to the final product quality, were met. A corresponding process control, however, is not practical, since measuring the effects of certain processes may require relatively long measurement times, frequently ex situ, or may even necessitate the destruction of the sample. Moreover, immense effort, in terms of time and equipment, would have to be made on the metrology side to provide the required measurement results. Additionally, utilization of the process tool would be minimized since the tool would be released only after the provision of the measurement result and its assessment. Furthermore, many of the complex mutual dependencies of the various processes are typically not known, so that an a priori determination of respective "optimum" process specifications may be difficult.

The introduction of statistical methods, also referred to as statistical process control (SPC), for adjusting process parameters, significantly relaxes the above problem and allows a moderate utilization of the process tools while attaining a relatively high product yield. Statistical process control is based on the monitoring of the process output to thereby identify an out-of-control situation, wherein a causality relationship may be established to an external disturbance. After occurrence of an out-of-control situation, usually operator interaction is required to manipulate a process parameter to return to an in-control situation, wherein the causality relationship may be helpful in selecting an appropriate control action. Nevertheless, in total, a large number of dummy substrates or pilot substrates may be necessary to adjust process parameters of respective process tools, wherein tolerable parameter drifts during the process have to be taken into consideration when designing a process sequence, since such parameter drifts may remain undetected over a long time period or may not be efficiently compensated for by SPC techniques.

Recently, a process control strategy has been introduced and is continuously being improved, allowing enhanced efficiency of process control, desirably on a run-to-run basis, while requiring only a moderate amount of measurement data. In this control strategy, the so-called advanced process control (APC), a model of a process or of a group of interrelated processes, is established and implemented in an appropriately configured process controller. The process controller also receives information including pre-process measurement data and/or post-process measurement data as well as information related, for instance, to the substrate history, such as type of process or processes, the product type, the process tool or process tools in which the products are to be processed or have been processed in previous steps, the process recipe to be used, i.e., a set of required sub-steps for the process or processes under consideration, wherein, possibly, fixed process parameters and variable process parameters may be contained, and the like. From this information and the process model, the process controller determines a controller state or process state that describes the effect of the process or processes under consideration on the specific product, thereby permitting the establishment of an appropriate parameter setting of the variable parameters of the specified process recipe to be performed with the substrate under consideration.

Although significant advances in providing enhanced process control strategies have been made, process variations may nevertheless occur during the complex interrelated manufacturing sequences, which may be caused by the plurality of individual process steps, which may affect the various materials in a more or less pronounced manner. These mutual influences may finally result in a significant variability of material characteristics, which in turn may then have a significant influence on the final electrical performance of the semiconductor device under consideration. Due to the continuous shrinkage of critical feature sizes, at least in some stages of the overall manufacturing process, frequently, new materials may have to be introduced to adapt device characteristics to the reduced feature sizes. One prominent example in this respect is the fabrication of sophisticated metallization systems of semiconductor devices in which advanced metal materials, such as copper, copper alloys and the like, are used in combination with low-k dielectric materials, which are to be understood as dielectric materials having a dielectric constant of approximately 3.0 and significantly less, in which case these materials may also be referred to as ultra low-k dielectrics (ULK). By using highly conductive metals, such as copper, the reduced cross-sectional area of metal lines and vias may at least partially be compensated for by the increased conductivity of copper compared to, for instance, aluminum, which has been the metal of choice over the last decades, even for sophisticated integrated devices. On the other hand, the introduction of copper into semiconductor manufacturing strategies may be associated with a plurality of problems, such as sensitivity of exposed copper surfaces with respect to reactive components, such as oxygen, fluorine and the like, the increased diffusion activity of copper in a plurality of materials typically used in semiconductor devices, such as silicon, silicon dioxide, a plurality of low-k dielectric materials and the like, copper's characteristic of generating substantially no volatile byproducts on the basis of typically used plasma-enhanced etch processes, and the like. For these reasons, sophisticated inlaid or damascene process techniques have been developed in which typically the dielectric material may have to be patterned first in order to create trenches and via openings, which may then be coated by an appropriate barrier material followed by the deposition of the copper material. Consequently, a plurality of highly complex processes, such as the deposition of sophisticated material stacks for forming the interlayer dielectric material including low-k dielectrics, patterning the dielectric material, providing appropriate barrier and seed materials, filling in the copper material, removing any excess material and the like, may be required for forming sophisticated metallization systems wherein the mutual interactions of these processes may be difficult to assess, in particular, as material compositions and process strategies may frequently change in view of further enhancing overall performance of the semiconductor devices. Consequently, a thorough monitoring of the material characteristics may be required during the entire manufacturing sequence for forming sophisticated metallization systems in order to efficiently identify process variations, which may typically remain undetected despite the provision of sophisticated controlling and monitoring strategies, as described above.

With reference to FIGS. 1a-1b, typical process strategies of monitoring the characteristics of dielectric materials may be described in accordance with typical conventional process strategies.

FIG. 1a schematically illustrates a semiconductor device 100 in a manufacturing stage in which one or more material layers 110 are formed above a substrate 101. It should be appreciated that the substrate 101 may represent any appropriate carrier material for forming thereon and therein respective circuit elements, such as transistors, capacitors and the like, as may be required by the overall configuration of the device 100. The one or more material layers 110 may be formed at any appropriate manufacturing stage, for instance during a sequence for forming circuit elements in the device layer, i.e., in and above a semiconductor layer (not shown), or may be formed in the contact level or metallization level of the device 100. In the example shown in FIG. 1a, it may be assumed that the one or more material layers 110 may comprise a plurality of dielectric materials 110A, 110B, 110C which may, for instance, represent a complex material system as may be required for forming respective circuit elements or any other device features. For example, the dielectric layer 110A may represent a material, such as silicon dioxide, polycrystalline silicon and the like, which may be patterned on the basis of the layers 110B, 110C, which may represent an anti-reflective coating (ARC) layer and a photoresist material and the like. Thus, the material composition of the individual layers 110A, 110B, 110C may have a significant influence during the further processing of the device 100 and on the finally obtained electrical performance of the device 100. For instance, the material composition of the individual layers 110B, 110C may significantly affect the behavior during the lithography process for patterning the layer 110A. For instance, the index of refraction and the absorbance of the layers 110C, 110B and 110A with respect to an exposure wavelength may result in a certain optical response of the layers 110, which may be adjusted on the basis of the layer thickness of the individual layers 110. Consequently, during the deposition of the layers 110A, 110B, 110C, a respective process control may be applied so as to reduce process variations, which may result in an undesired variation of the material composition, while also the thickness of individual layers 110A, 110B, 110C may be controlled in order to maintain overall process quality. For this purpose, non-destructive optical measurement techniques are available, such as ellipsometry and the like, in which the optical thickness of the individual layers 110C, 110A, 110A may be determined, possibly after each deposition step, by using an appropriate probing optical beam 102A, which may contain any appropriate wavelength, and detecting a reflected or refracted beam 102B. Consequently, by the optical measurement process based on the beams 102A, 102B, inline measurement data may be provided to enhance process control for forming the dielectric layers 110. However, the conventionally applied optical measurement techniques may provide information about material characteristics which may vary in a more or less step-like manner, such as a pronounced change of the index of refraction at interfaces between the various layers 110A, 10B, 110C, which may be very convenient in determining the optical thickness of the materials 110 but which may not provide information with respect to a more or less gradually varying material characteristic of one or more of the layers 110. For example, it may be very difficult to determine a gradual variation within one of the layers 110 in different semiconductor devices or device areas on the basis of conventionally applied optical measurement techniques.

FIG. 1b schematically illustrates the semiconductor device 100 according to a further example in which the plurality of dielectric materials 110 may represent one or more materials of an interlayer dielectric material of a metallization system 120. For example, the layers 110 may comprise a dielectric material 110E, which may be provided in the form of a low-k dielectric material, a "conventional" dielectric material such as fluorine-doped silicon dioxide and the like, while a further dielectric material 110D may represent a low-k dielectric material, which may differ in composition from the layer 110E or which may represent substantially the same material, depending on the overall process strategy. Furthermore, as previously explained, a trench 110F may be formed in the layer 110D and a via opening 110G may be provided in the dielectric material 110E. Furthermore, in the manufacturing stage shown, a barrier layer 121 may be formed on exposed surface portions of layers 110D, 110E. For instance, the barrier layer 121 may be comprised of tantalum, tantalum nitride and the like, which are frequently used barrier materials in combination with copper.

The semiconductor device 100 as shown in FIG. 1b may be formed in accordance with well-established damascene strategies in which the layers 110E, 110D, possibly in combination with an etch stop layer 111, may be deposited by any appropriate deposition technique. During the corresponding process sequence for forming the layers 110E, 110D, optical measurement techniques may be used, for instance on the basis of the above-described concepts, in order to provide measurement data for controlling layer thickness and the like. Thereafter, the openings 110F, 110G may be formed by appropriate patterning regimes, which may involve lithography processes, resist removal processes, etch steps, cleaning steps and the like, thereby resulting in a more or less pronounced exposure of the layers 110D, 110E to various process conditions, which may have an influence on at least exposed portions of the materials 110E, 110D. For example, low-k dielectrics and in particular ultra low-k dielectric materials may be sensitive to a plurality of chemical components, which may typically be applied during the various processes, such as resist removal processes, etch processes, cleaning processes and the like. Consequently, a certain degree of material modification or damaging may occur in the layer 110D and/or the layer 110E, depending on the overall process strategy. Consequently, during the further processing, for instance by providing the barrier layer 121, the modified material composition in the dielectric material 110 may result in different process conditions and possibly also in different material characteristics of the barrier layer 121, thereby also affecting the further processing. For example, the material modification or damaging of the layer 110D may result in a reduced adhesion and/or diffusion blocking effect of the barrier material 121, which may compromise the overall reliability of the metallization system 120. In other cases, during the removal of excess material of the copper and the barrier material 121 after the electrochemical deposition of the copper material, the damaged areas of the layer 110D may have an influence on the removal conditions, which in turn may also negatively affect the overall characteristics of the resulting metallization system 120.

It is thus important to monitor respective material modifications during the process sequence for forming the metallization system 120 which, however, may be very difficult on the basis of optical inline measurement techniques, as may be used for determining characteristics such as layer thickness and the like, as previously explained with reference to FIG. 1a. The situation becomes even more complex when the material modification is to be determined for patterned devices since the patterning processes as well as the geometry of the feature elements to be formed in the layers 110 may also affect the degree of material modification, since during the patterning process a plurality of additional process conditions may be "seen" by the materials 110, which may result in a different degree of material modification compared to non-patterned structures. Since the degree of material modification may gradually vary due to even minor process variations during the complex sequence of manufacturing processes involved, in particular in patterned device structures, it may be extremely difficult to obtain a quantitative measure of the degree of damage on the basis of optical measurement techniques used in a conventional context. For this reason, frequently, external measurement techniques may be used, which may typically involve destructive analysis techniques, such as cross-sectional analysis by electron microscopy and the like, in order to obtain information on the degree of material modification within the material layers 110. However, due to the destructive nature of the analysis techniques involved, only a very limited amount of measurement data may be gathered, thereby contributing to a less efficient overall process control. Furthermore, due to the external analysis technique including sophisticated sample preparation and the like, a significant amount of delay may be involved in obtaining the measurement data, thereby also contributing to a less efficient control mechanism for the manufacturing sequence for forming the metallization system 120.

The present disclosure is directed to various methods and systems that may avoid, or at least reduce, the effects of one or more of the problems identified above.

SUMMARY OF THE INVENTION

The following presents a simplified summary of the invention in order to provide a basic understanding of some aspects of the invention. This summary is not an exhaustive overview of the invention. It is not intended to identify key or critical elements of the invention or to delineate the scope of the invention. Its sole purpose is to present some concepts in a simplified form as a prelude to the more detailed description that is discussed later.

Generally, the present disclosure relates to techniques and systems for determining material characteristics in a quantitatively highly resolved manner by using non-destructive measurement techniques which provide sensitivity to the chemical composition of material layers, such as dielectric materials, during a manufacturing sequence for forming semiconductor devices. For this purpose, measurement data may be obtained from a plurality of substrates, possibly in combination with respective reference data, to establish a relation between measurement parameters, such as appropriate wavelengths of an optical probing beam and the like, and at least one material characteristic, wherein the relation may enable a quantitative estimation of the material characteristic for other semiconductor substrates by determining respective measurement values for the measurement parameters determined upon establishing the relation. Consequently, the non-destructive measurement techniques may be applied inline, that is, at any appropriate manufacturing stage within the manufacturing environment, thereby significantly enhancing the monitoring of material characteristics by non-destructive measurement techniques, such as Fourier transformed infrared spectroscopy and the like, and reducing any delay between obtaining a quantitative assessment of a material characteristic of interest and processing respective substrates, while also providing enhanced flexibility in selecting appropriate measurement samples. The relation may be efficiently established by using sophisticated data analysis techniques, such as partial least square algorithms (PLS), classical least square algorithms (CLS), principle component analysis (PCA) and regression (PCR) and the like, thereby providing efficient data reduction and selection of relevant measurement parameters.

One illustrative method disclosed herein comprises obtaining a first measurement data set by a non-destructive measurement technique from one or more first substrates having formed thereabove one or more first layers of one or more materials of the semiconductor device, wherein the first measurement data set contains a plurality of measured parameters conveying information about at least one structural characteristic of the one or more first layers. The method further comprises obtaining reference data related to the one or more first layers and determining a model on the basis of a subset of the measured parameters of the first measurement data set, wherein the model reflects a relationship of the subset of parameters and the reference data. Furthermore, the method comprises obtaining a second measurement data set from one or more second substrates having formed thereabove one or more second layers of the one or more materials, wherein the second measurement data set corresponds at least to the subset. Finally, the method comprises evaluating the at least one structural characteristic of the one or more second layers on the basis of the model and the second measurement data set.

A further illustrative method disclosed herein relates to monitoring of a material characteristic of one or more material layers in a semiconductor manufacturing process sequence. The method comprises establishing a relation between the material characteristic to a number of measurement parameters by using first measurement data containing information about a chemical composition of the one or more material layers and performing a data reduction technique. The method additionally comprises obtaining second measurement data during the semiconductor manufacturing process sequence by a non-destructive measurement process, wherein the non-destructive measurement process provides measured values of at least the number of measurement parameters. Finally, the method comprises determining a quantitative measure of the material characteristic by using the measured values and the relation.

One illustrative system disclosed herein is an inline system for determining material characteristics during semiconductor production. The system comprises an interface configured to receive measurement data containing information about a chemical composition of one or more materials provided above substrates comprising semiconductor devices in an intermediate manufacturing stage. The system further comprises a model unit containing a model relating the measurement data to a material specific parameter so as to indicate a gradual variation of the chemical composition. Furthermore, the system comprises an evaluation unit configured to output a predicted value of the material specific parameter on the basis of the measurement data and the model.

BRIEF DESCRIPTION OF THE DRAWINGS

The disclosure may be understood by reference to the following description taken in conjunction with the accompanying drawings, in which like reference numerals identify like elements, and in which.

Figure 1A:
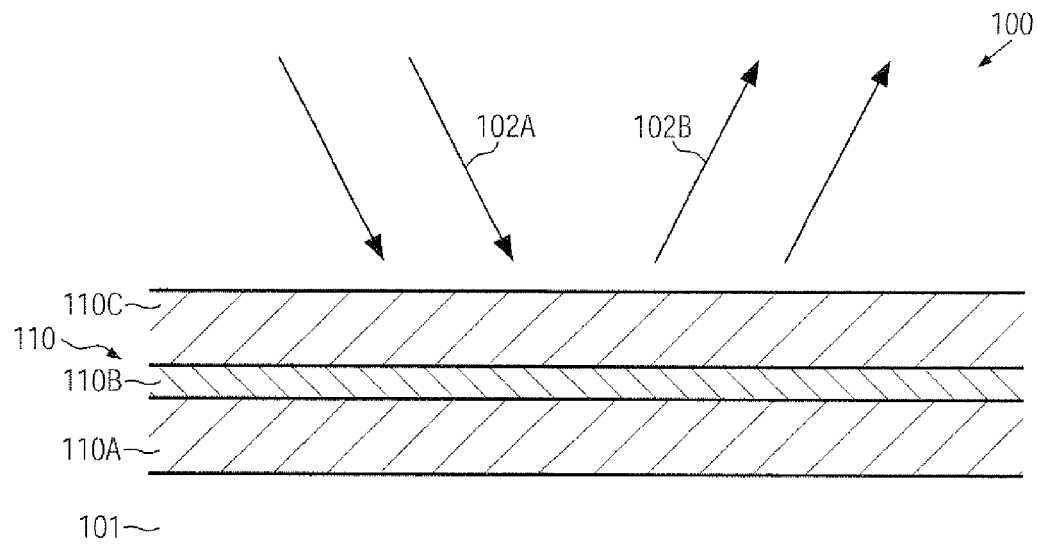
FIG. 1a schematically illustrates a cross-sectional view of a semiconductor device having formed thereon one or more dielectric material layers, the layer thickness of which may be determined inline on the basis of conventional optical measurement techniques.
Figure 1B:
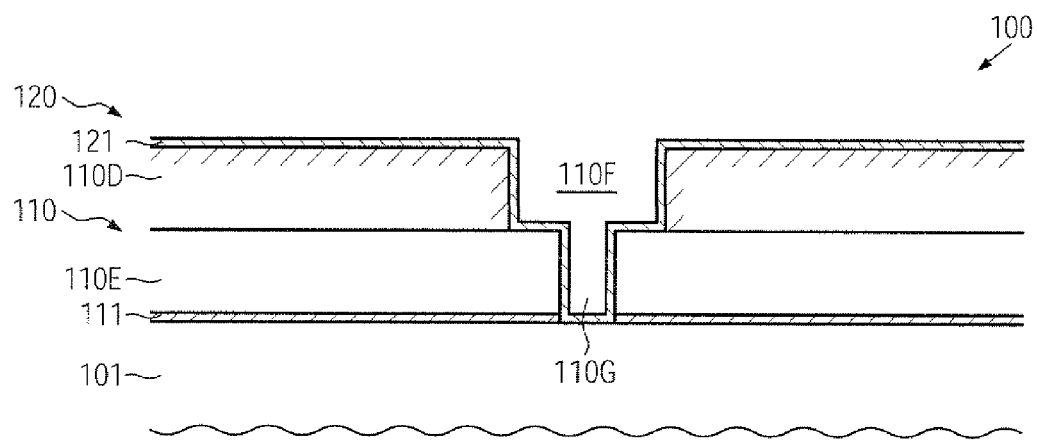
FIG. 1b schematically illustrates the conventional semiconductor device with a patterned dielectric material for a metallization system, wherein a degree of material modification in the dielectric material, such as a low-k dielectric material, may be determined on the basis of external destructive analysis techniques.

While the subject matter disclosed herein is susceptible to various modifications and alternative forms, specific embodiments thereof have been shown by way of example in the drawings and are herein described in detail. It should be understood, however, that the description herein of specific embodiments is not intended to limit the invention to the particular forms disclosed, but on the contrary, the intention is to cover all modifications, equivalents, and alternatives falling within the spirit and scope of the invention as defined by the appended claims.

DETAILED DESCRIPTION

Various illustrative embodiments of the invention are described below. In the interest of clarity, not all features of an actual implementation are described in this specification. It will of course be appreciated that in the development of any such actual embodiment, numerous implementation-specific decisions must be made to achieve the developers' specific goals, such as compliance with system-related and business-related constraints, which will vary from one implementation to another. Moreover, it will be appreciated that such a development effort might be complex and time-consuming, but would nevertheless be a routine undertaking for those of ordinary skill in the art having the benefit of this disclosure.

The present subject matter will now be described with reference to the attached figures. Various structures, systems and devices are schematically depicted in the drawings for purposes of explanation only and so as to not obscure the present disclosure with details that are well known to those skilled in the art. Nevertheless, the attached drawings are included to describe and explain illustrative examples of the present disclosure. The words and phrases used herein should be understood and interpreted to have a meaning consistent with the understanding of those words and phrases by those skilled in the relevant art. No special definition of a term or phrase, i.e., a definition that is different from the ordinary and customary meaning as understood by those skilled in the art, is intended to be implied by consistent usage of the term or phrase herein. To the extent that a term or phrase is intended to have a special meaning, i.e., a meaning other than that understood by skilled artisans, such a special definition will be expressly set forth in the specification in a definitional manner that directly and unequivocally provides the special definition for the term or phrase.

Generally, the present disclosure relates to methods and systems enabling a more efficient monitoring and, in some illustrative aspects disclosed herein, controlling of manufacturing processes on the basis of a determination of characteristics of materials which may be formed and/or treated during a specific sequence of manufacturing processes in fabricating semiconductor devices. To this end, non-destructive measurement techniques may be applied at any appropriate stage of the manufacturing sequence under consideration in order to "probe" one or more materials with respect to structural characteristics, i.e., material characteristics, which are associated with the chemical composition that may gradually vary within the material, depending on the process conditions prevailing during the preparation of the semiconductor substrate for receiving the one or more materials and/or during the formation of the respective one or more materials and/or during a subsequent treatment thereof, for instance in the form of patterning, cleaning and the like. For example, as previously explained, a plurality of different dielectric materials may typically have to be used in the form of permanent materials of the semiconductor device, as sacrificial layers, for instance in the form of polymer materials, resist materials and the like, the composition of which may change during the progress of the manufacturing sequence, wherein a more or less gradual change of the material characteristics may also provide a quantitative indication with respect to the quality of the manufacturing processes involved. Many characteristics of dielectric materials may be substantially determined by the chemical composition thereof, i.e., the presence of certain atomic species and the chemical bonds established within the material, so that many types of reaction with the environment, such as chemical interaction, mechanical stress, optical interaction, heat treatments and the like, may result in a modification of the molecular structure, for instance by re-arranging chemical bonds, breaking up chemical bonds, introducing additional species in a more or less pronounced degree and the like. Consequently, the status of the one or more materials under consideration may therefore represent the accumulated history of the processes involved, thereby enabling efficient monitoring and, if desired, efficient control of at least some of the involved manufacturing processes. The structural information, i.e., the information represented by the molecular structure of the materials under consideration, may at least partially be made available to observation by selecting appropriate probing techniques, wherein, in the present disclosure, non-destructive techniques may be applied to enable an inline monitoring of material characteristics and thus manufacturing processes. In this respect, an inline metrology process may be considered as a process technique in which a corresponding sample substrate may be maintained within the manufacturing environment, thereby avoiding any transport activities to external metrology stations. Preferably, the measurement performed within the manufacturing environment may not substantially negatively influence any semiconductor devices formed on the sample substrate, so that the sample substrate may still be used as a product substrate during the further processing. As will be described later on in more detail, a plurality of metrology techniques may be provided by the teaching of the present disclosure, which may enable a quantitative evaluation of at least one material characteristic with a significantly reduced delay compared to conventional strategies for evaluating material characteristics, while, in some illustrative embodiments, respective probing measurement processes may be associated with a corresponding manufacturing process, thereby further reducing the overall delay for obtaining an evaluation of a material characteristic and associated manufacturing processes.

As is well known, chemical bonds in a plurality of materials may have excited states in the form of oscillations and rotations, the energy levels of which may correspond to the energy of infrared radiation. Thus, by introducing infrared radiation of appropriate wavelength into a material of interest, certain oscillations and rotations may be excited, depending on the various species, the chemical bonds between the species, the concentration of certain species, the wavelength range of the incoming infrared radiation and the like. Upon exciting respective oscillations and rotations, a more or less amount of infrared radiation, depending on the material, may be absorbed, which may therefore result in a modified spectrum of the infrared radiation leaving the material under consideration. Consequently, due to the absorption of a specific amount of the incoming radiation, the resulting infrared radiation may contain information about structural characteristics, such as the presence of certain species, the concentration thereof, the status of chemical bonds and the like, which may also reflect the status of a manufacturing sequence, as explained above. According to the principles disclosed herein, this information with respect to structural characteristics of the one or more materials under consideration may be efficiently "extracted," at least partially, by applying efficient data analysis techniques which may be accomplished by establishing a relation, that is, a model, that represents a quantitative correlation between appropriately selected measurement parameters, for instance an intensity value of one or more wavelength components with a specified material characteristic.

For example, as previously indicated, low-k dielectric materials may frequently be used in metallization systems of advanced semiconductor devices wherein overall performance of the metallization system may depend on one or more characteristics of the low-k dielectric material, such as a degree of modification or damaging occurring during the formation and processing of the low-k dielectric material, the degree of porosity, the presence of unwanted atomic species and the like. A corresponding status of the low-k dielectric materials of different substrates and even of different device regions within the same substrate may thus be determined by a gradual distribution of one or more material parameters, which may be efficiently determined on the basis of the principles disclosed herein. For example, the depth of a damaged region of a low-k dielectric material may represent a material parameter which may have a significant influence on the overall performance of the corresponding metallization system. As previously explained, a corresponding depth of damaging of a low-k dielectric material may be caused by a plurality of processes, which may thus also be evaluated on the basis of a quantitative measure of the corresponding material characteristic, such as a depth of damaging. In other cases, a degree of porosity, the presence of unwanted material species and the like, may represent respective material parameters which may be evaluated in order to obtain an efficient monitoring of the overall process sequence. In other cases, the amount of optical energy deposited in a resist layer may represent a material parameter which may be efficiently monitored by the techniques disclosed herein in order to evaluate the status of a lithography process.

In some illustrative aspects disclosed herein, an appropriate set of measurement parameters may be determined on the basis of efficient data reduction techniques, such as principle component analysis (PCA), partial least square analysis (PLS) and the like, which may thus enable the identification of prominent measurement parameters, such as appropriate wavelengths or wave numbers, which may convey most of the required information with respect to the structural characteristics of the materials under consideration. These efficient statistical data processing algorithms may thus be used to obtain a significant reduction of the high dimensional parameter space, i.e., in the case of an infrared spectrum, the large number of wavelengths involved, while substantially not losing valuable information on the intrinsic characteristics of the materials. For example, a powerful tool for evaluating a large number of measurement data, for instance in the form of intensities relating to a large number of parameters, is the principle component analysis which may be used for efficient data reduction in order to establish an appropriate model on the basis of a reduced number of measurement parameters. For instance, during the principle component analysis, appropriate measurement parameters, for instance wave numbers, may be identified which may be correlated with a high degree of variability with respect to respective reference data, which may, for instance, be provided by other measurement techniques in order to obtain reference data for the material characteristic under consideration. For instance, destructive or any other analysis techniques may be used, for instance in the form of electron microscopy, Auger electron spectroscopy (AES), secondary ion mass spectroscopy (SIMS), x-ray diffraction and the like, in order to obtain the reference data. Thus, by identifying a reduced number of measurement parameters, i.e., wavelengths or wave numbers, corresponding to the highest degree of variability with respect to the reference data, an efficient model with high statistical relevance may be established which may then be used for quantitatively evaluating measurement data obtained during the manufacturing process, thereby enabling inline monitoring and possibly controlling of one or more of the processes involved.

Similarly, powerful statistical analysis tools may be used, such as PLS, from which representative portions of a spectrum may be identified, and an appropriate regression model may be created in combination with appropriate reference data, thereby also enabling efficient inline monitoring and/or controlling of processes by using the model with measurement data obtained by non-destructive metrology techniques.

In still other illustrative embodiments, other analysis techniques may be used, such as CLS (classical least square) regression, in which reference spectra may be obtained for each component of a material system, such as for each sub-layer of a complex layer stack and the like, which may then be combined to provide an appropriate model, which may then be used for evaluating gradual changes in the layer stack.

Thus, appropriate models may be established for a specific situation in the manufacturing sequence under consideration for providing the possibility of inline monitoring of processes and materials, wherein the respective models may thus implicitly take into account the complexity of the response to the probing radiation, for instance with respect to the plurality of species, contained in the layer stack, the structure of the sampled device region and the like. In other illustrative aspects disclosed herein, other non-destructive measurement techniques may be used in combination with statistical analysis techniques in order to establish appropriate models for at least one material characteristic under consideration. For instance, Auger electron spectroscopy, secondary ion mass spectroscopy, x-ray diffraction and the like may provide structural information with respect to one or more material layers, which may then be used for establishing an appropriate model, as explained above.

Figure 2A:
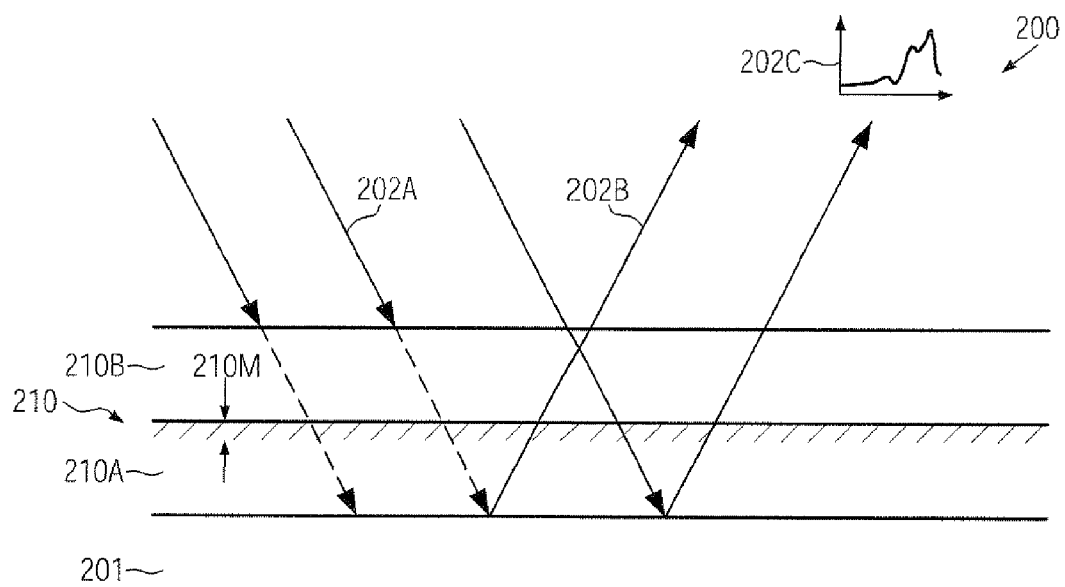
FIGS. 2a-2c schematically illustrate cross-sectional views of a semiconductor device during various manufacturing stages in providing a dielectric material, such as an interlayer dielectric material including low-k dielectrics, wherein information of a gradually varying degree of material modification may be obtained on the basis of optical measurement techniques, according to illustrative embodiments.

FIG. 2a schematically illustrates a cross-sectional view of a semiconductor device 200 which may comprise a substrate 201 that may represent any appropriate carrier material for forming therein and thereon circuit elements of sophisticated semiconductor devices. For example, the substrate 201 may comprise an appropriate base material, such as a semiconductor material, an insulating material and the like, above which may be formed a semiconductor layer, such as a silicon-based layer, a germanium layer, a semiconductor layer having incorporated therein any appropriate species for obtaining the desired electronic characteristics and the like. For convenience, any such semiconductor layer is not explicitly shown in FIG. 2a. Furthermore, the semiconductor device 200 may comprise, in the manufacturing stage shown, one or more materials 210, such as dielectric materials having a reduced dielectric constant and the like, a characteristic of which may be evaluated in a quantitative manner, as will be explained later on in more detail. The one or more materials 210 may be provided in any configuration as may be required for the further processing of the semiconductor device 200. That is, the one or more materials 210 may represent a material in which a specific characteristic may vertically and/or laterally vary, depending on the overall process history of the semiconductor device 200. In the embodiment shown, the one or more materials 210 may be provided in the form of a layer stack including layers 210A, 210B, which may differ in material composition, layer thickness and the like. It should be appreciated, however, that the one or more materials 210 may not be restricted to a stack of layers including two sub-layers 210A, 210B, but may represent any dielectric material which may be patterned or which may be substantially globally formed across the entire substrate 201, depending on the manufacturing stage under consideration. Furthermore, the one or more materials 210 may comprise three or more sub-layers, one or more of which may be provided in a locally restricted manner, depending on the overall requirements. As previously discussed, the quantitative evaluation of a material characteristic that may gradually vary, such as a thickness of a modified zone 210M, the degree of modification therein, such as the density of a certain species, the density of specific type of chemical bonds, and the like may be accomplished on the basis of complex analysis techniques, which may typically involve a destruction of the sample according to conventional approaches. According to the principles disclosed herein, at least one parameter related to the modified zone 210M, such as a thickness thereof and the like, may be determined by using appropriate non-destructive techniques and appropriately analyzing the resulting response. For this purpose, in some illustrative embodiments, a probing beam 202A may be used in the form of infrared radiation, thereby allowing the probing of the one or more materials 210 on the basis of the molecular structure, as previously explained. Hence, a corresponding optical response 202B may have encoded therein information with respect to the modified zone 210M. For example, a spectrum 202C obtained on the basis of the response 202B may be different with respect to a spectrum of the incoming beam 202A due to the complex interaction of the infrared radiation of the beam 202A with the one or more materials 210. That is, the absorption at specific wavelengths or wavelength ranges may be modified due to the presence of the material 210 wherein also the modified zone 210M may cause a respective modification, thereby providing quantitative information with respect to one or more characteristics of the modified zone 210M.

Figure 2B:
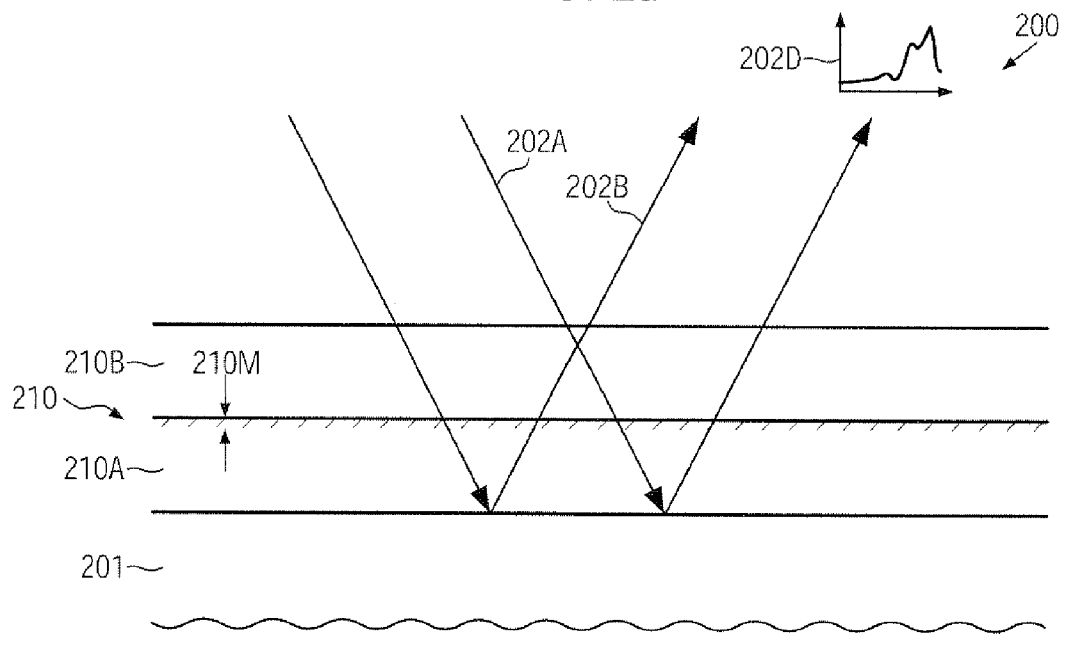

FIG. 2b schematically illustrates the semiconductor device 200 in which the modified zone 210M may have a different status compared to a situation as shown in FIG. 2a, which may be caused, for instance, by a further treatment of the device 200, while, in other cases, the semiconductor devices 200 of FIGS. 2a and 2b may represent equivalent devices at different areas of the substrate 201 or the devices 200 may be located at different substrates. Consequently, when exposed to the probing beam 202A, the respective response 202B may result in a spectrum 202D that may have incorporated information with respect to the zone 210M which may have a different status, for instance, with respect to a reduced thickness and the like.

Figure 2C:
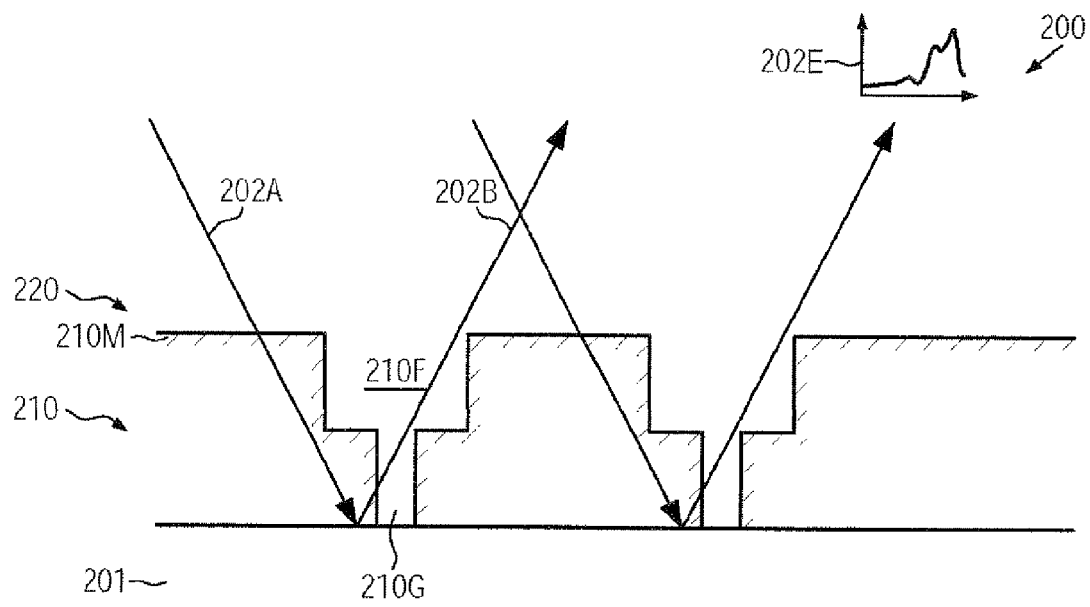

FIG. 2c schematically illustrates the semiconductor device 200 according to further illustrative embodiments in which the one or more materials 210 may represent a dielectric material for a metallization system 220. The semiconductor device 200 as shown in FIG. 2c may, for instance, represent the device 200 in an advanced manufacturing stage compared to FIGS. 2a and 2b, while, in other cases, the material 210 of FIGS. 2a and 2b may be provided in a different device level compared to the metallization system 220 as shown in FIG. 2c. For example, the material 210 may be patterned so as to have openings 210F, 210G, for instance in the form of a trench and a via opening, respectively, as may frequently be the case in dual damascene strategies for forming metal lines and vias of the metallization system 220. It should be appreciated, however, that the one or more materials 210 may be provided in any appropriate patterned state, depending on the overall process strategy. Furthermore, the material 210 may comprise the modified portion 210M, at least partially, which may be caused by any preceding manufacturing processes, such as etch processes, cleaning processes and the like, as is also previously explained. Also, in this case, one or more characteristics of the modified zone 210M may be determined, for instance a thickness thereof, a degree of modification and the like, by using the probing beam 202A to obtain the optical response 202B, wherein a corresponding structural information may be contained in a spectrum 202E, which may have a specific "modulation" due to the configuration of the material 210. Consequently, the status of the modified zone 210M may also provide valuable information on the quality of one or more processes performed for providing the device 200 as shown in FIG. 2c.

Thus, the semiconductor devices 200 of FIGS. 2a-2c represent examples of various situations in which at least one material characteristic of the one or more materials 210 may gradually vary depending on the process strategy involved. That is, in the examples shown, a thickness of the modified zone 210M may be used as an indicator of the status of one or more process techniques while, in other cases, a gradual variation of the material composition and the like may be used to quantify the status of the material 210 and thus of one or more of the processes involved. Consequently, any process sequence may be used for forming the semiconductor devices 200, which may include well-established process techniques, as are also previously described with reference to the device 100. Contrary to conventional approaches, however, inline measurement data may be obtained, for instance in the form of the spectra 202C, 202D, 202E, in order to provide a quantitative evaluation of the one or more materials 210.

To this end, in one illustrative embodiment, the probing beam 202A may be obtained on the basis of a Fourier transformed infrared spectroscopy technique (FTIR), in which, typically, a specific wavelength range may be provided by an appropriate illumination source, wherein a corresponding output radiation, such as the probing beam 202A, may be modulated by interferometry, in which a difference in path length of a first portion and a second portion of the infrared radiation is continuously varied, for instance by using a beam splitter and a continuously moving reflective element in one part of the optical path. Thus, upon recombining a portion of the infrared beam passing through a substantially stable optical path, a portion of the initial infrared beam passing through a continuously varying optical path, the corresponding modulated combined beam may be efficiently used as a probing beam, such as the beam 202A, which may also be referred to as an interferogram. Upon directing the modulated beam onto a sample, such as the semiconductor devices 200, the resulting interferogram may thus comprise the required information with respect to the material 210 due to the corresponding absorbance that is determined by the present status of the materials as explained above. The corresponding interferogram of the optical response 202B may be efficiently converted into a spectrum by Fourier transformation, wherein the corresponding spectrum may then be used for further data analysis to extract the desired information and thus obtain a value for quantitatively characterizing the material characteristic under consideration, such as a degree of modification of the zone 210M, such as a thickness thereof and the like. Providing the probing beam 202A in the form of an interferogram with a subsequent data processing in the form of a Fourier transformation may thus enable the gathering of spectra as non-destructive measurement data. In this manner, the well-known inherent advantages of FTIR spectroscopy may be exploited, wherein a desired high fraction of the total energy of the infrared source may be continuously used for probing the sample under consideration, such as the semiconductor device 200. Furthermore, due to the usage of an interferogram, the sample may be probed with a plurality of wavelengths at the same time, thereby also simultaneously obtaining the response intensity of the respective wavelength components of the spectra 202C, 202D, 202E, and providing enhanced signal-to-noise ratio, wherein the required modification of the probing beam 202A may also be accomplished at very short times, since only moderately small changes of the optical path lengths may be required for generating the probing beam 202A in the form of an interferogram. Hence, in addition to an increased signal-to-noise ratio, a reduced overall measurement time may be realized, thereby enabling efficient inline measurements, which may even be performed for individual process chambers of a process tool. For example, respective spectra may be obtained within milliseconds, thereby providing the potential for generating the corresponding measurement data without influencing the overall throughput of a corresponding manufacturing sequence.

After obtaining the non-destructive measurement data 202C, 202D, 202E, an evaluation of the material characteristic under consideration may be obtained on the basis of a corresponding model relating at least some of the measurement data with the material characteristic under consideration, as will be described later on in more detail.

Figure 2D:
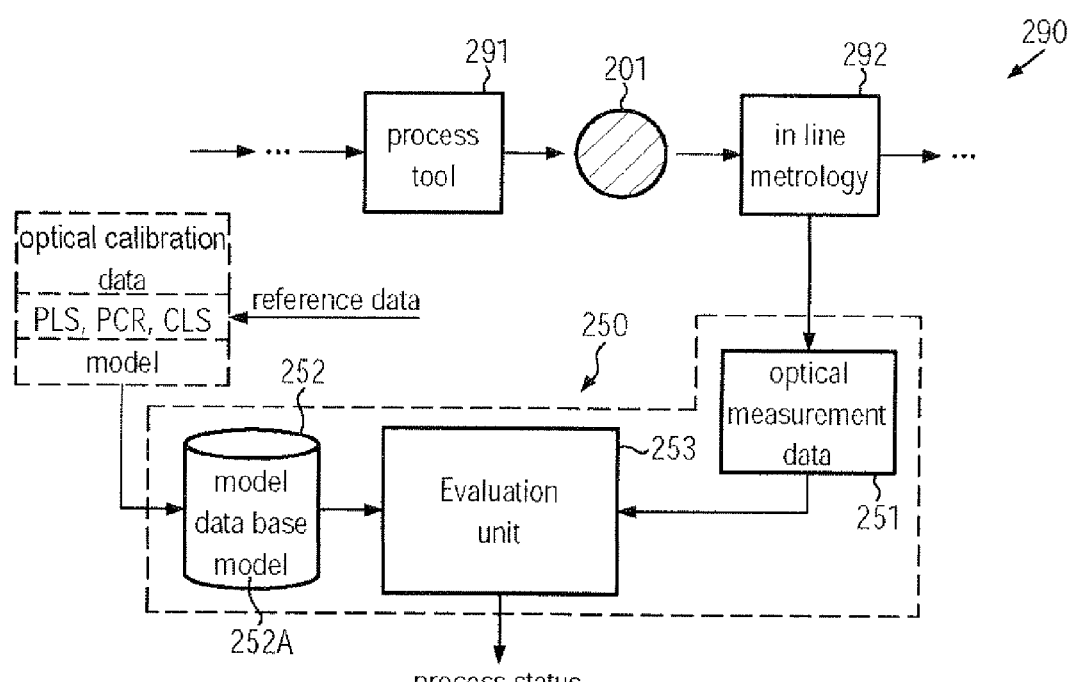
FIG. 2d schematically illustrates a system for evaluating material characteristics, such as a degree of modification or damaging of the dielectric material on the basis of optical inline measurement techniques, according to illustrative embodiments.

FIG. 2d schematically illustrates a manufacturing environment 290 that is configured to perform at least one manufacturing process for processing semiconductor devices. The manufacturing environment 290 may thus comprise one or more process tools 291, in which respective substrates, such as the substrates 201, may be processed in accordance with the overall process strategy, such as the deposition of layers such as the layers 210, patterning the same by lithography, performing etch processes, cleaning processes and the like, as previously explained. Furthermore, the environment 290 may comprise an inline metrology tool 292, which may be configured to provide structural measurement data, for instance in the form of optical measurement data 202C, 202D, 202E, as previously explained. In other cases, the metrology tool 292 may provide any type of measurement data, which may contain information with respect to the molecular structure of one or more materials under consideration, such as the materials 210, as previously explained. For example, the inline metrology tool 292 may comprise equipment for performing a Fourier transformed infrared spectroscopy process (FTIR), as previously explained. Moreover, the manufacturing environment 290 may comprise a system 250 configured to determine the status of a dielectric material and/or of a process performed in the environment 290, which may affect one or more material layers of the substrate 201, such as the materials 210. The system 250 may comprise an interface 251 for receiving respective inline measurement data, such as optical measurement data in the form of spectra and the like. Moreover, the system 250 may comprise a model database 252, which may include at least one model adapted to the process situation of the environment 290 for evaluating at least one material characteristic, as previously explained. The at least one model 252A may represent a regression model obtained on the basis of calibration data, which may be provided in the form of inline metrology measurement data obtained from specified "calibration" samples, for which a value for the at least one material characteristic may be known in advance. For instance, respective reference data may be obtained by appropriate analysis techniques, such as cross-sectional analysis by electron microscopy, for instance for defining a size of a damage zone of low-k dielectric materials, such as the modified zone 210M, as previously explained, and the like. The calibration data, possibly in combination with the reference data, may then be analyzed by statistical algorithms, such as PLS, PCR, CLS, in order to identify a correlation of parts of the calibration data with the reference data. Based on the identified relevant measurement data, a model may be established which may then be stored in the database 252.

The system 250 may further comprise an evaluation unit 253, which may be coupled to the interface 251 to obtain the optical measurement data and which may also be coupled to the database 252 in order to select an appropriate model 252A corresponding to the process situation for which the measurement data are received by the interface 251. Based on the model 252A and measurement data, a numerical value or any other indication may be determined that specifies the material characteristic under consideration. For example, the evaluation unit 253 provides a gradually varying value based on the model 252A and the inline measurement data, such as the spectra 202C, 202D, 202E, that corresponds to the present state of the material(s) of interest, wherein the model predicted value may be provided with a reduced delay, thereby enabling an efficient estimation of the status of the environment 290, while also providing the potential for controlling one or more processes of the environment 290, as will be described later on in more detail.

Figure 2E:
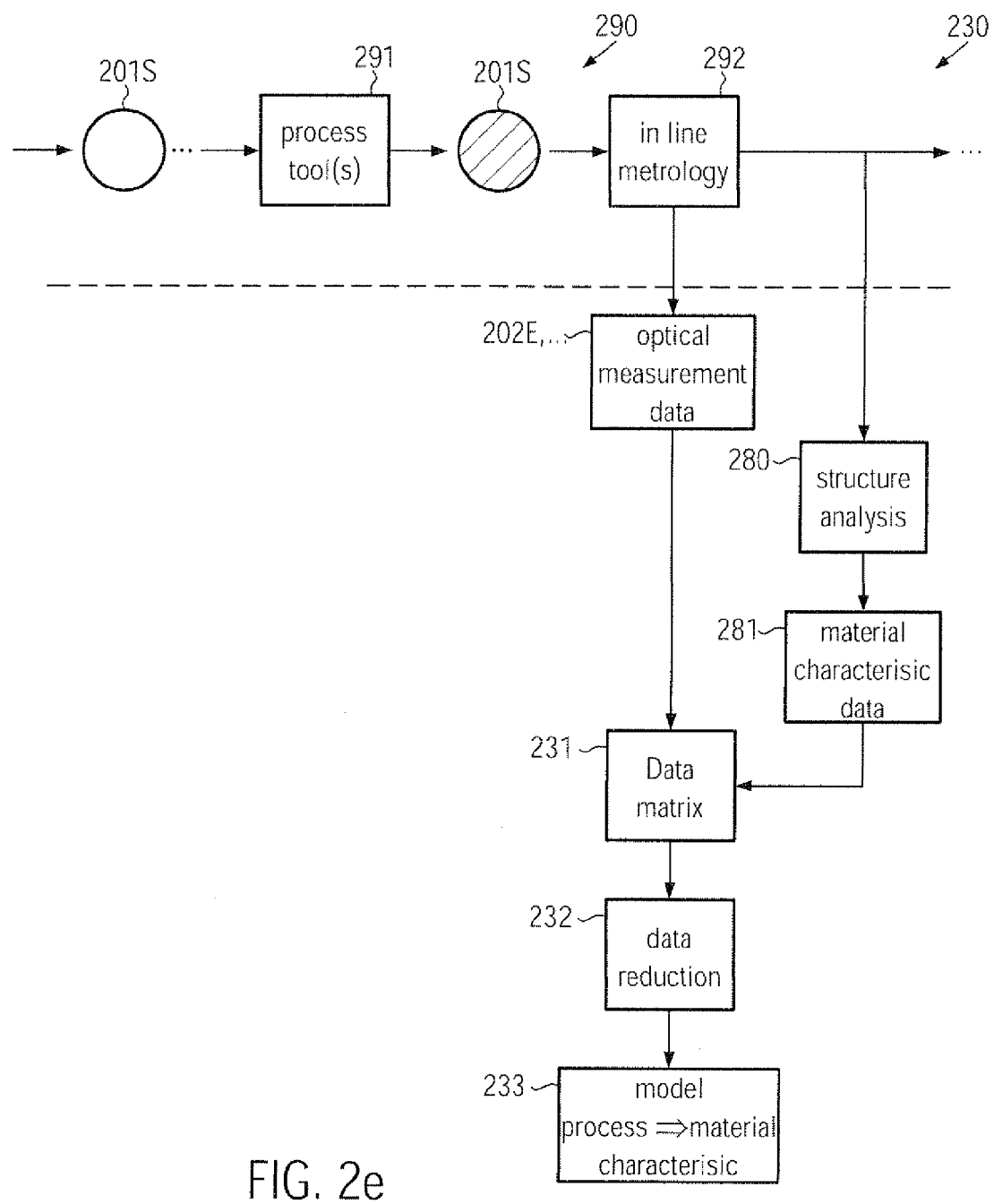
FIG. 2e schematically illustrates a process sequence including a process for establishing a model for monitoring gradually varying material characteristics on the basis of inline measurement techniques, according to further illustrative embodiments.

FIG. 2*e* schematically illustrates a process sequence 230 for establishing the one or more models 252A adapted to a specific situation in the environment 290. As illustrated, one or more sample substrates 201S may be processed in the environment 290 according to a specified process situation. That is, the sample substrates 201S may be processed under substantially similar conditions as corresponding product substrates, thereby providing a high degree of authenticity of respective inline measurement data, such as optical measurement data 202E, . . . obtained by the inline metrology tool 292. It should be appreciated that, upon processing the sample substrate 201S in the inline metrology tool 292, different measurement conditions may be applied, for instance with respect to the wavelength range used for the probing beam 202A and the like. After collecting the inline measurement data 202E, . . . , at least some of the sample substrates 201S may be subjected to a structural analysis, for instance in the form of a destructive measurement technique, as previously described. For this purpose, any appropriate measurement tool 280 may be used, which may typically be provided outside of the manufacturing environment 290. Based on the structural analysis in the metrology tool 280, respective reference data or material characteristic data 281 may be generated, which may, for instance, represent numerical values of a respective material characteristic under consideration, for instance a thickness of a modified zone, such as the zone 210M, a degree of modification and the like. Consequently, an appropriate reference data may be available, at least for some of the inline measurements 202E, . . . . Thereafter, a data analysis may be performed with respect to the reference data 281 and the measurement data 202E, . . . , which may be accomplished on the basis of any appropriate analysis technique, such as partially least square techniques, principle component analysis techniques, classical least square techniques and the like. For example, in a first stage 231 of the data analysis, a data matrix may be determined on the basis of at least the measurement data 202E, . . . , for instance if a classical least square algorithm may be considered wherein the respective measurement data 202E, . . . may comprise the optical spectra of each individual component of the material mixture under consideration. In other illustrative embodiments, the data matrix may also comprise the reference data 281. Upon applying efficient statistical analysis techniques, the data matrix may be used to identify a correlation of a variance of the measurement data 202E, . . . with a variance of the reference data 281, which may be accomplished by well-established matrix operations. For example, in the step 231, respective wavelengths or wave numbers of the spectra 202E, . . . may be determined which may have a pronounced correlation to the reference data 281, thereby indicating the most relevant measurement parameters, i.e., wavelength or wave numbers of the optical measurement data 202E, . . . .

For example, in principle component analysis, the eigenvalues or eigenvectors of the co-variance matrix of the measurement data may be determined, wherein the eigenvalues may thus represent the degree of correlation of the respective variances of the optical measurement data and the related reference data 281.

In some illustrative embodiments, a data reduction may be performed in the stage 232, which is to be understood as identifying respective measurement parameters of the measurement data 202E, i.e., respective wavelength ranges or wavelengths, which substantially determine the corresponding reference data, which represents the process result of the manufacturing sequence in the environment 290. Hence, a reduced number of measurement parameters may be selected, substantially without losing any information about the structural characteristics of the sample substrates 201S. In a next step 233, a model may be established, for instance by using linear regression, wherein the corresponding measurement values of the measurement parameters identified in the step 232 may thus be related to a respective process result in the form of the corresponding reference data 281. For example, as previously indicated, the model may relate measurement values in the form of measured intensities or the measured absorbance at a specific wavelength to the numerical value of the process result, i.e., the material characteristic under consideration. The respective coefficients of the regression, which may also be referred to as regression vector and the like, may be determined on the basis of measurement data obtained from the sample substrate 201S and the reference data 281 and may be used later on in providing a numerical value for the material characteristic under consideration when assessing measurement data from actual product substrates.

Figure 2F:
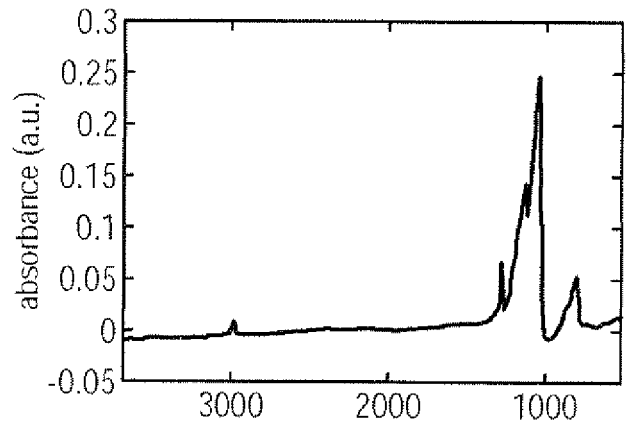
FIGS. 2f-2g schematically illustrate measurement data in the form of a Fourier transformed infrared interferogram and a corresponding selection of meaningful measurement parameters which may be used in establishing a model according to illustrative embodiments.

FIG. 2*f* schematically illustrates a representative spectrum 202C, 202D, 202E, which may be obtained by an FTIR technique. In the example shown, the vertical axis may represent the absorbance in arbitrary units that may be obtained when directing the probing beam 202A in the form of an interferogram to the one or more materials of interest, as previously explained. The response may be Fourier transformed so as to obtain the spectrum as shown in FIG. 2*f*.

Figure 2G:
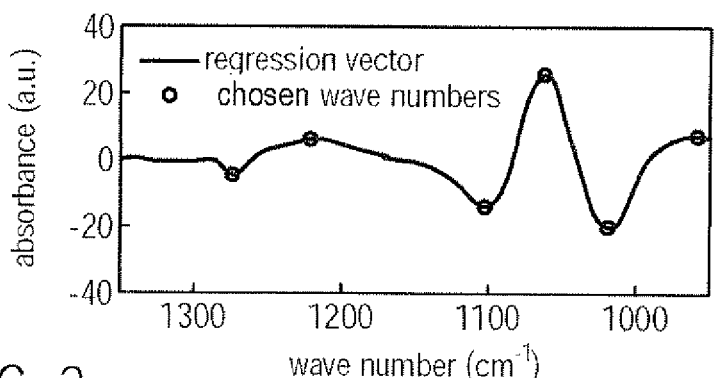

FIG. 2*g* schematically illustrates the result of the steps 231 and 232 according to a PLS strategy in which the multi-dimensional parameter space may be searched for a direction correlating the variance of the measurement data, i.e., the spectrum of FIG. 2f, with a set of reference values, i.e., the reference data 281. The first coordinate of the determined direction in the multi-dimensional parameters space, which may also be referred to as regression vector, may correlate with the variance of the optical measurement data and the reference values 281.

FIG. 2g schematically illustrates the regression vector for the most relevant part of the spectrum of FIG. 2f, i.e., the portion of the spectrum of FIG. 2f from approximately 1350-950 cm$^{-1}$. As is evident from FIG. 2g, the amount of correlation with the variance of the reference values 281 may significantly vary so that, according to one illustrative embodiment, a significant parameter reduction may be applied without losing substantial information with respect to the structural configuration of the material of interest. In one illustrative embodiment, a corresponding selection of appropriate measurement parameters may be accomplished by identifying local minima and maxima in the progression of the regression vector and selecting pairs of a local minimum and a local maximum as potential candidates for establishing the corresponding model. For example, the local minimum and maximum pairs may be ordered by size, starting with the pair of maximum size. For example, the wave number corresponding to the most pronounced local maximum at approximately 1060 cm$^{-1}$ in combination with the left neighboring local minimum at approximately 1100 cm$^{-1}$ may be used to select corresponding measurement data for obtaining a first estimate for the regression coefficients. If the corresponding regression equation of the model based on the first estimate of the regression coefficients may result in a non-sufficient prediction of the corresponding reference value, additional maximum/minimum pairs may be added to the model in order to finally obtain a desired degree of matching with the reference data. For example, using the three maximum/minimum pairs as indicated in FIG. 2g, corresponding regression coefficients may be determined and may be used for predicting the material characteristics, such as a thickness of a damage zone, such as the modified zone 210M, as previously explained.

The quality of the model obtained by increasingly adding pairs of local minima/maxima may be tested by comparing the predicted values for the material characteristic under consideration, such as the depth of the damage zone, with reference values by calculating, for instance, the root mean square error of prediction (RMSEP). In this manner, the desired degree of "convergence" between the reference values and the predicted values may be adjusted by using the minimum number of minimum/maximum pairs without resulting in an "overfitting," which may otherwise result in increased statistical error.

Figure 2H:
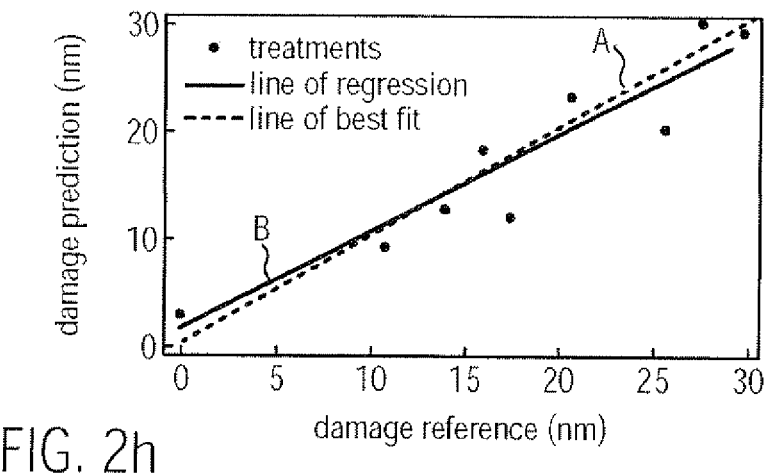
FIG. 2h schematically illustrates a comparison between quantitative predictions of a model obtained on the basis of measurement data and quantitative measurement values obtained on the basis of cross-sectional analysis techniques, according to illustrative embodiments.

FIG. 2h schematically illustrates a comparison of reference data obtained by destructive analytical techniques, such as AES or SIMS measurements taken at various depth positions of a sample in the form of thickness of a damage zone, wherein the varying depths are indicated by the horizontal axis. The corresponding measurement results are illustrated as individual data points, while a line of best fit for these data points, represented by curve A, is also illustrated. On the other hand, curve B represents the damage prediction obtained on the basis of the model that has been established by using PLS and the selected parameters, i.e., wave numbers, as indicated in FIG. 2g. Thus, as is evident from FIG. 2h, the predictions of the model, represented by curve B, substantially coincide with the prediction obtained by the measurement values represented by curve A.

It should be appreciated that, in other cases, an appropriate selection of measurement parameters, for instance of appropriate wave numbers, which may be incorporated into the model, may be accomplished depending on the analysis technique used. For instance, if applying a principle component analysis in which the covariance matrix of the data, i.e., in the examples shown above, the spectra 202C, 202D, 202E, and the reference data 281 may be diagonalized, that is, the eigenvalues may be determined, respective eigenvalues and eigenvectors may be selected as appropriate measurement parameters. Also, in this case, the number of measurement parameters to be used for establishing the model may be adjusted by comparing the prediction of the model with respective reference data for a different number of eigenvectors incorporated into the corresponding model. For example, a linear model may be used in which the value of a feature to be determined, such as the degree of material modification and the like, may then be determined on the basis of the measurement values and the corresponding coefficients, which in turn may be determined during the process of building a model by using appropriate measurement data and corresponding reference data, as previously explained. Equation 1 illustrates an example of a linear regression model for a multivariate regression.

$$p = b_0 + bX + e \qquad \text{Equation 1}$$

Here, p represents the value of the feature of interest, such as a material characteristic, and the like, $b_0$ represents the intercept, b the slope and e the residues, i.e., statistically distributed errors. During the calibration phase, i.e., during establishing the model, the unknown coefficient vectors $b_0$ and b as well as the normally distributed residues e are unknown and may be determined by a least square algorithm, in which representatives for the vectors $b_0$ and b are determined that make the quadratic difference: $(p-(b_0+b))^2$ minimal. Consequently, once respective representatives for the coefficient vectors $b_0$, b have been determined, the desired characteristic p may be calculated for subsequent measurements, that is, non-destructive measurement data, such as the spectra 202C, which may be obtained for substrates other than the substrates used for establishing the model according to Equation 1.

Figure 2I:
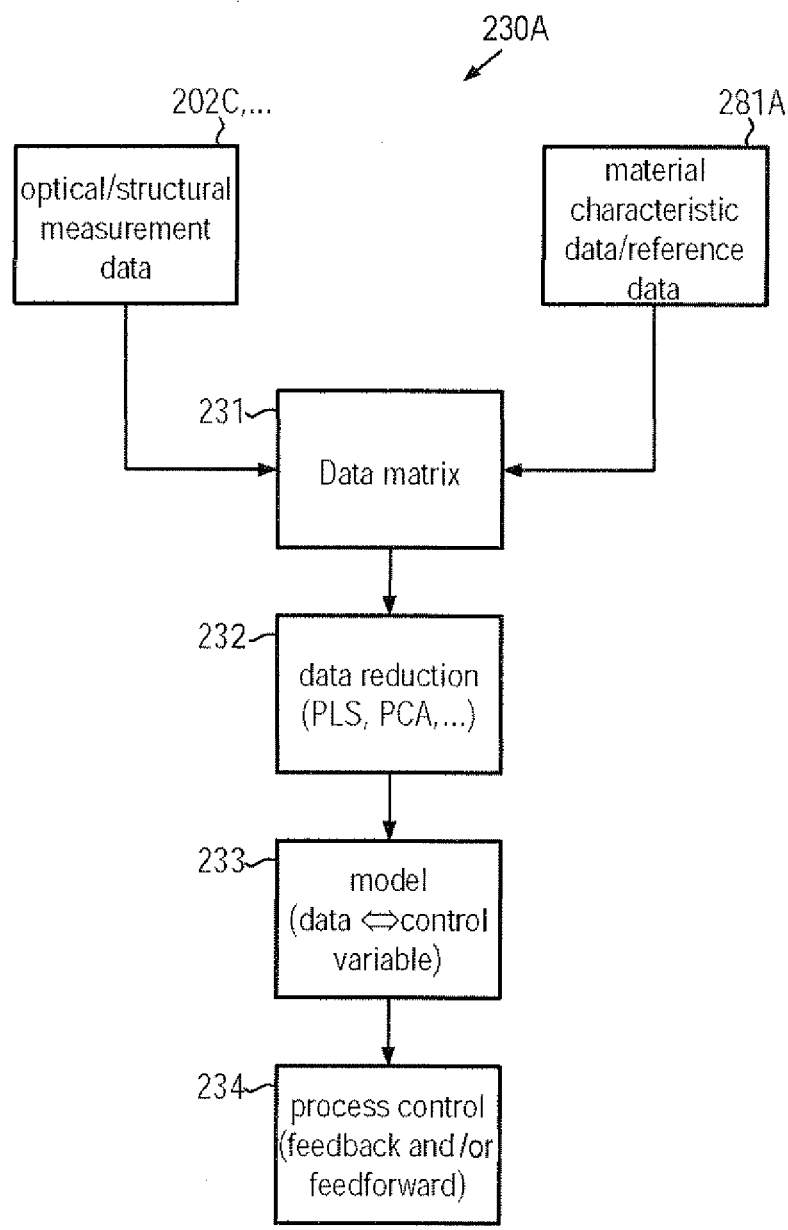
FIG. 2i schematically illustrates a sequence of activities for providing enhanced process control on the basis of data analysis techniques in combination with optical measurement data for determining one or more appropriate measurement variables that may be used for feedback and/or feed forward process control, according to further illustrative embodiments.

FIG. 2i schematically illustrates a further process sequence in which an appropriate model may be established on the basis of the same strategies as previously described, wherein the corresponding characteristic feature described by the model may be used for controlling one or more manufacturing processes. For this purpose, in step 231, measurement data and reference data may be acquired, indicated as data matrix, wherein respective optical or structural measurement data, such as the spectra 202C . . . , and appropriate reference data 281A may be obtained. The reference data 281A may represent material characteristic data, as for instance previously explained, which may indicate a specific material characteristic or a device specific characteristic, such as a critical dimension, when this characteristic is correlated to the molecular structure of the one or more materials of interest. For example, as will be described later on in more detail, the material modification in a photochemically responsive material may be correlated with the finally obtained critical dimension and hence this dimension may be used as reference data for establishing an appropriate model correlating the optical measurement data with a critical dimension. In still other illustrative embodiments, the reference data may be represented by tool specific parameters, such as exposure dose used for modifying a photoresist material and the like. In this case, the corresponding model may correlate the measurement data directly with a control variable of the respective process tool, thereby providing an additional mechanism for controlling one or more manufacturing processes. In step 232, an appropriate data reduction may be accomplished, as is also previously described with reference to the process sequence 230, and thereafter a model may be established in step 233, which may provide a relation between an appropriate characteristic and the optical measurement data 202C..., wherein, as previously explained, even the specific characteristic may represent a control variable which may be directly used for controlling one or more process tools. In step 234, a process control may be performed on the basis of values of the specific characteristic predicted by the model established in step 233, wherein the process control may be performed as a feedback control and/or a feed forward control, depending on the process requirements.

Figure 2J:
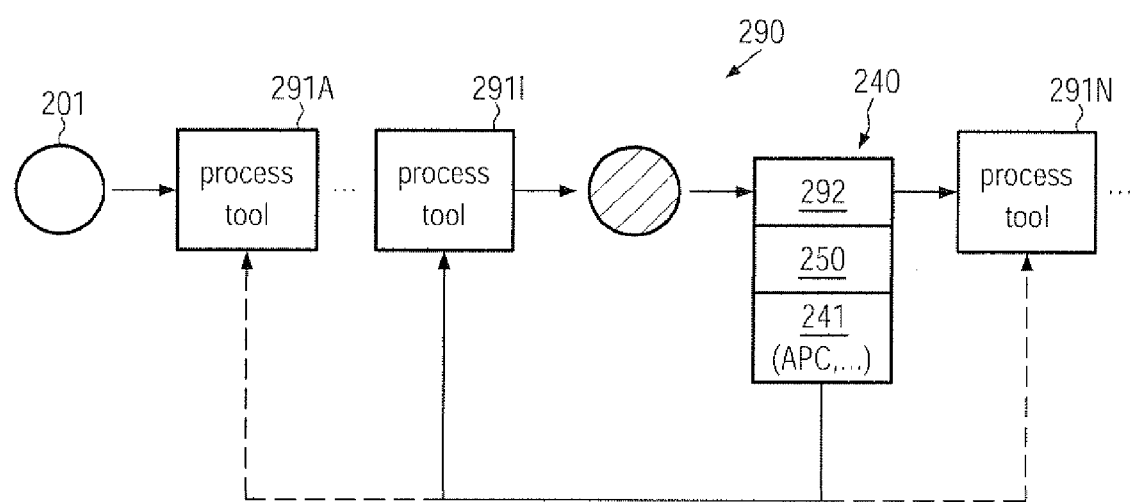
FIG. 2j schematically illustrates a manufacturing environment for performing a process sequence in which at least one manufacturing step may be controlled on the basis of inline measurement relating to a gradually varying material characteristic, such as the degree of material damage, according to still further illustrative embodiments.

FIG. 2j schematically illustrates the manufacturing environment 290 in which, additionally or alternatively to the monitoring of one or more material characteristics, as previously described, a control strategy may be implemented according to the sequence 230A. As illustrated, the manufacturing environment may comprise one or more process tools 291A ... 291N, which may perform a sequence of manufacturing processes which may have a more or less pronounced influence on the one or more materials of interest, such as the materials 210, as previously described. Furthermore, the manufacturing environment 290 may comprise an inline control system 240 which may include a metrology tool, such as the tool 292 in combination with the system 250, which in turn is operatively connected to a controller unit 241. The system 250 may have substantially the same configuration as previously described with reference to FIG. 2d, wherein an appropriate model may be used to predict values for a specific characteristic, which may be used for controlling one or more of the process tools 291A ... 291N. For example, the process tool 291I may represent one or more process chambers for performing an etch process or a cleaning process or a combination thereof for patterning the material 210, as previously described, wherein a process variation in the tool 291I may have an influence on the damage zone or modified zone 210M, which may thus also influence the further processing of the substrates 201. In this case, the thickness of the modified zone may be used as specific material characteristic, which may be delivered to the control unit 241 which may have implemented therein an appropriate control mechanism in which the model predicted characteristic may be used as a measurement of the process output of the tool 291I, which may then be compared with a target value in order to re-adjust tool internal parameters. In other illustrative embodiments, the specified characteristic predicted by the model of the system 250 may be used for controlling other tools, such as the process tool 291N in a feed forward configuration, and/or other tools may be controlled, such as the tool 291A, by appropriately re-adjusting the respective tool specific parameters. By selecting an appropriate specific characteristic, such as the degree of modification, the depth of the damage zone and the like, the quality of the process results of each of the tools 291A ... 291N may be monitored and, if desired, controlled since the specific model predicted characteristic may be considered as a general parameter for characterizing the quality of the various processes, even if these processes are very different from each other. In this case, one or more of the process tools 291A ... 291N may be controlled on the basis of an internal control loop according to conventional control strategies, such as APC (advanced process control) techniques, while additionally the control unit 241 may establish a further control loop, thereby acting as a fine tuning control instance, which may detect even subtle process variations of the entire sequence in the environment 290 and may thus appropriately re-adjust the respective target values of the individual control loops.

In other illustrative embodiments, the model in the system 250 may predict values for control variables which may be directly used as input for the controller 241 so as to re-adjust the respective tool settings. For example, the specific characteristic predicted by the model of the system 250 may represent the flow rate of a gas component, or any other parameter for establishing an etch ambient and the like, so that a more direct control of respective process tools may be accomplished.

It should be appreciated that monitoring and/or controlling of one or more of the processes in the environment 290 on the basis of non-destructive measurement data may be accomplished in a highly efficient manner in that the metrology tool 292 may be positioned at any appropriate stage of the process sequence within the environment 290. For example, as previously explained, FTIR measurements may be obtained in a very time efficient manner on the basis of available equipment, which may even be connected to respective process tools or process chambers in order to obtain the respective measurement data substantially without any delay. The corresponding metrology tool 292 may be specifically adapted to obtain the inline measurement data, for instance by obtaining measurement data for the measurement parameter, previously determined when establishing the respective model, as previously explained, or by obtaining full range spectra and the like.

Figure 2K:
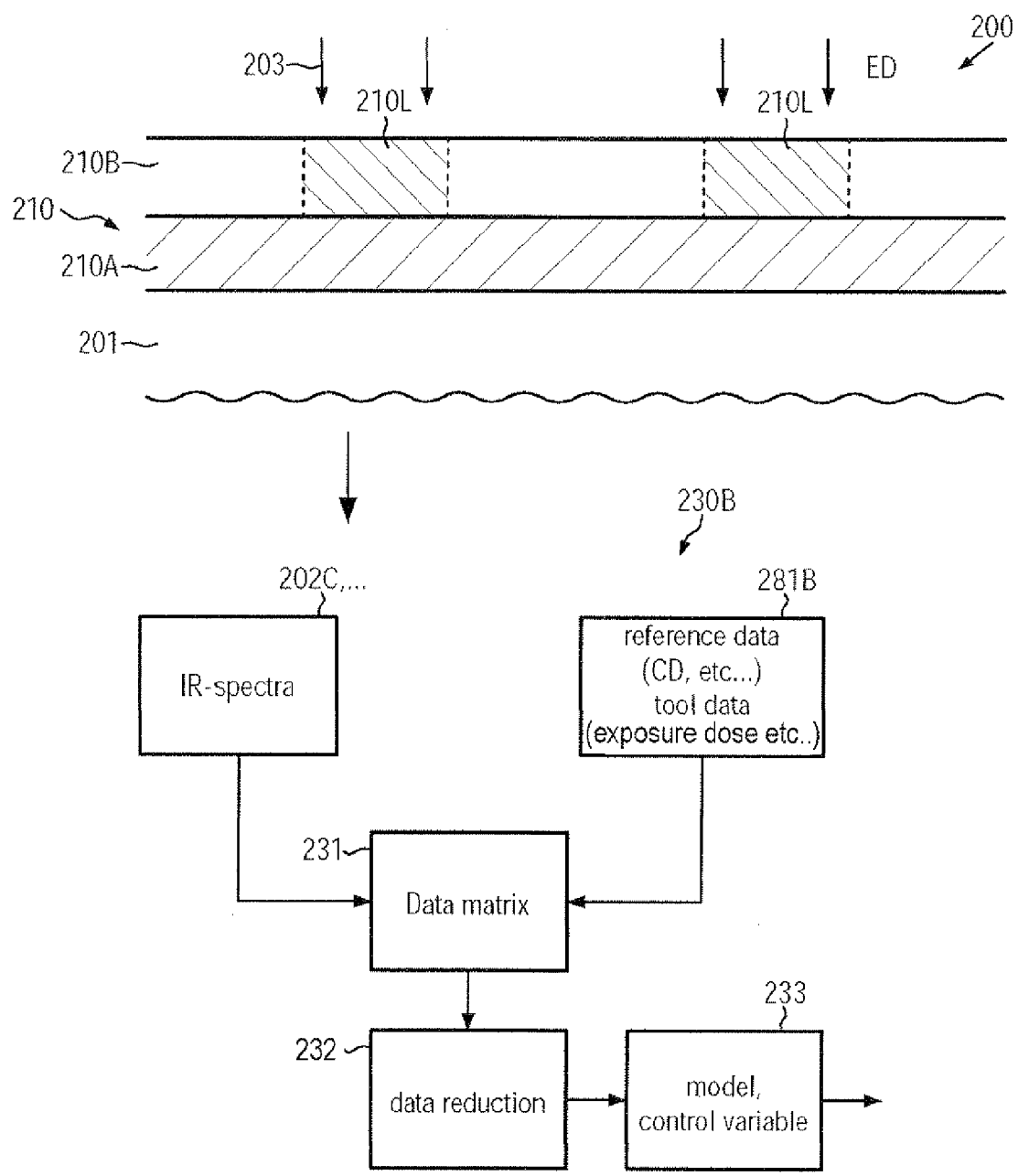
FIG. 2k schematically illustrates a process strategy for monitoring the characteristics of a photoresist material during an exposure process, according to yet other illustrative embodiments.

FIG. 2k schematically illustrates the semiconductor device 200 according to still further illustrative embodiments in which the one or more materials 210 of interest may comprise material layers 210A, 210B, wherein the layer 210B may represent a photochemically reactive material, such as a photoresist and the like. Hence, during an exposure process 203, certain portions of the material 210B may be exposed and hence the photochemical reaction may create modified portions therein, which may represent latent images 210L. The characteristics of the layer 210B, i.e., the characteristics of the latent images 210L, may depend on the specific photomask and the exposure conditions, such as exposure dose used, thickness of the layer 210B and the like. Consequently, the result of the exposure process 203, possibly in combination with any pre- and post-exposure processes, may be represented by the degree of modification of the layer 210B, which may be determined by infrared spectroscopy, as previously explained. Thus, a process sequence 230C may be applied, in which respective infrared spectra, such as the spectra 202C ... as previously described, and appropriate reference data 281B, may be used in order to establish an appropriate model for monitoring and possibly controlling the exposure process 203. For instance, the reference data 281B may represent a critical dimension of the resist layer 210B after development so that, upon the corresponding infrared spectra obtained immediately after the exposure process 203, an expected critical dimension of the latent images 210L may be predicted prior to actually performing a development process. In other cases, the reference data 281B may include tool specific data, such as the exposure dose used during the process 203 and the like. The data 202c ... and the reference data 281B may be acquired in step 231 and may be processed in step 232, as previously described, so as to finally obtain a model in step 233, which may thus enable the prediction of a specific characteristic, such as a CD of the developed resist, an exposure dose and the like, on the basis of inline measurement data. That is, by predicting the expected critical dimension of the latent images 210L prior to actually performing a development process, a re-adjustment of exposure parameters may be initiated or an additional exposure may be performed if an under-exposure may be predicted by the model created in step 233. In this way, enhanced exposure performance may be obtained, while significantly reducing any efforts in reworking incorrectly exposed substrates.

As a result, the present disclosure provides techniques and systems in which non-destructively obtained measurement data, such as infrared spectra and the like, may be obtained during a manufacturing process and may be evaluated with respect to gradually changing material characteristics, thereby enabling enhanced monitoring and/or controlling of one or more processes. By using powerful data analysis techniques, such as PCR, PLS, CLS and the like, in combination with measurement techniques providing structural information, gradually varying material characteristics may be determined during semiconductor fabrication, thereby also enabling the monitoring of complex manufacturing sequences. For instance, the material characteristics of sensitive dielectric materials, such as ULK material, may be detected, for instance with respect to an extension of a damage zone, in order to monitor the quality of metallization systems of sophisticated semiconductor devices. The inline measurement data may be obtained on the basis of infrared spectroscopy, for instance using FTIR and the like, while also other measurement techniques, such as AES, SIMS, XRD and the like, may be used, some of which may even allow directly obtaining the measurement data at process chambers, substantially without affecting the overall process throughput. In other cases, additionally or alternatively, control mechanisms may be implemented by using the values predicted by the models obtained by the techniques disclosed herein, thereby enhancing overall process performance.

The particular embodiments disclosed above are illustrative only, as the invention may be modified and practiced in different but equivalent manners apparent to those skilled in the art having the benefit of the teachings herein. For example, the process steps set forth above may be performed in a different order. Furthermore, no limitations are intended to the details of construction or design herein shown, other than as described in the claims below. It is therefore evident that the particular embodiments disclosed above may be altered or modified and all such variations are considered within the scope and spirit of the invention. Accordingly, the protection sought herein is as set forth in the claims below.

What is claimed:

1. A method, comprising:
   obtaining, at a computer system, a first measurement data set by a non-destructive measurement technique from one or more first substrates having formed thereabove one or more first layers of one or more materials of a semiconductor device, said first measurement data set containing a plurality of measured parameters conveying information about at least one structural characteristic of said one or more first layers;
   obtaining, at the computer system, a reference data related to said one or more first layers, wherein the reference data is acquired from one or more third substrates using a second measurement technique;
   selecting, using the computer system, a subset of said measured parameters of said first measurement data set, wherein the subset is a reduced number of said measured parameters that correspond to high degrees of variability with respect to the reference data;
   determining, using the computer system, a model on the basis of said subset and said reference data, said model determining numerical values of said at least one structural characteristics as a function of measured values of said subset;
   obtaining, at the computer system, a second measurement data set from one or more second substrates having formed thereabove one or more second layers of said one or more materials, said second measurement data set corresponding at least to said subset; and
   determining, using the computer system, numerical values of said at least one structural characteristic of said one or more second layers on the basis of said model and said second measurement data set.

2. The method of claim 1, wherein the reference data is obtained by performing a second measurement technique comprising at least one of an Auger electron spectroscopy process, an x-ray diffraction process and a secondary ion mass spectroscopy process.

3. The method of claim 1, wherein said first measurement data set is obtained by performing an optical infrared based metrology process, and wherein selecting said subset of the measured parameters comprises selecting at least one pair of a local minimum and a local maximum in a progression of a regression vector corresponding to wavelengths in a spectrum used by the optical infrared based metrology process.

4. The method of claim 3, wherein performing said optical infrared based metrology process comprises performing a Fourier transformed infrared spectroscopy process.

5. The method of claim 1, wherein said one or more materials comprise a low-k dielectric material acting as an interlayer dielectric material of a metallization system of said semiconductor device.

6. The method of claim 1, wherein said one or more materials comprise a photochemical material.

7. The method of claim 1, wherein evaluating said at least one structural characteristic comprises determining a measure for a variation of a chemical composition of said one or more materials.

8. The method of claim 7, wherein said measure for a variation of a chemical composition specifies a degree of modification of an initial state of said one or more materials after performing at least one manufacturing process in the presence of said one or more materials.

9. The method of claim 8, wherein said degree of modification relates to a degree of damage created in said one or more materials.

10. The method of claim 1, wherein determining said model comprises applying at least one of a partial least square technique, a principal component technique and a classical least square technique to said first measurement data set.

11. The method of claim 10, wherein selecting said subset of measured parameters comprises performing a data reduction on said first measurement data set so as to identify appropriate representatives of said subset of measured parameters.

12. The method of claim 1, further comprising determining one or more control variables of one or more manufacturing processes used to further process said one or more second substrates on the basis of said evaluated at least one structural characteristic.

13. The method of claim 1, further comprising determining one or more control variables of one or more manufacturing processes used to form said one or more materials on one or more third substrates on the basis of said evaluated at least one structural characteristic.

14. The method of claim 1, wherein the non-destructive measurement technique comprises optical spectroscopy, and wherein the second measurement technique is a destructive measurement technique.

15. A method of monitoring a material characteristic of one or more material layers in a semiconductor manufacturing process sequence, the method comprising:

establishing, using a computer system, a relation between numerical values of said material characteristic and values of a number of measurement parameters by using first measurement data containing information about a chemical composition of said one or more material layers and performing a data reduction technique to select the number of measurement parameters from said first measurement data comprising a larger number of measurement parameters, wherein the values of the selected number of measurement parameters correspond to high degrees of variability with respect to reference data acquired from at least one sample substrate using a destructive measurement technique;

obtaining, at the computer system, second measurement data during said semiconductor manufacturing process sequence by a non-destructive measurement process, said non-destructive measurement process providing measured values of at least said number of measurement parameters; and determining, using the computer system, numerical values of said material characteristic by using said measured values and said relation.

16. The method of claim 15, wherein performing said data reduction technique comprises performing at least one of a classical least square technique, a partial least square technique and a principal component technique.

17. The method of claim 15, wherein said first and second measurement data are obtained by a non-optical measurement process.

18. The method of claim 15, wherein said first and second measurement data are obtained by using an optical measurement technique including a plurality of measurement wavelengths in the infrared wavelength range, and wherein performing the data reduction technique comprises selecting at least one pair of a local minimum and a local maximum in a progression of a regression vector corresponding to the plurality of wavelengths in the infrared wavelength range.

19. The method of claim 18, wherein using said optical measurement technique comprises performing a Fourier transformed infrared spectroscopy measurement.

20. The method of claim 15, wherein establishing said relation further comprises acquiring the reference data indicating a quantitative measure of said material characteristic from said at least one sample substrate using the destructive measurement technique and determining a correlation of said reference data with said first measurement data to determine said number of measurement parameters.

21. The method of claim 15, wherein said semiconductor manufacturing process sequence comprises forming a metallization system of semiconductor devices on the basis of said one or more material layers.

22. The method of claim 21, wherein said one or more material layers comprise a low-k dielectric material.

23. A method, comprising:

accessing, at a computer system, optical measurement data acquired over a plurality of wavelengths from a plurality of substrates processed in an environment according to a specified process situation, said optical measurement data indicating at least one structural characteristic of the substrates;

accessing, at the computer system, structural analysis data acquired by applying destructive measurement techniques to at least one of the plurality of substrates;

identifying, using the computer system, a subset of the plurality of wavelengths representing local maxima and local minima in a correlation of said optical measurement data to said structural analysis data;

determining, using the computer system, a model on the basis of said subset and said structural analysis data, said model determining numerical values of said at least one structural characteristic as a function of measured values of said subset; and controlling, using the computer system, processing of subsequent substrates in the environment based on the model and optical measurement data acquired at the subset of the plurality of wavelengths.

24. The method of claim 23, wherein accessing the optical measurement data comprises accessing optical measurement data acquired by performing a Fourier transformed infrared spectroscopy process.

25. The method of claim 23, wherein accessing said structural analysis data comprises accessing structural analysis data indicating a depth of a damaged region of a low-K dielectric material deposited on the plurality of substrates.

26. The method of claim 23, wherein identifying the subset comprises selecting at least one pair of wavelengths corresponding to a local minimum and a local maximum in a progression of a regression vector formed based on the optical measurement data and the structural analysis data.

* * * * *